United States Patent
Fricke et al.

(10) Patent No.: US 9,540,431 B2
(45) Date of Patent: Jan. 10, 2017

(54) INHIBITORS OF THE CD95 SIGNALING PATHWAY FOR TREATMENT OF MDS

(71) Applicant: APOGENIX GmbH, Heidelberg (DE)

(72) Inventors: Harald Fricke, Mannheim (DE); Michaela Fontenay, Paris (FR); Claudia Kunz, Lustadt (DE)

(73) Assignee: Apogenix AG, Heidelberg (DE)

(*) Notice: Subject to any disclaimer, the term of this patent is extended or adjusted under 35 U.S.C. 154(b) by 0 days.

(21) Appl. No.: 14/415,851

(22) PCT Filed: Jul. 18, 2013

(86) PCT No.: PCT/EP2013/065245
§ 371 (c)(1),
(2) Date: Jan. 20, 2015

(87) PCT Pub. No.: WO2014/013036
PCT Pub. Date: Jan. 23, 2014

(65) Prior Publication Data
US 2015/0166632 A1    Jun. 18, 2015

(30) Foreign Application Priority Data

Jul. 18, 2012  (EP) .................................. 12176974

(51) Int. Cl.
| | |
|---|---|
| *A61K 38/18* | (2006.01) |
| *C07K 14/705* | (2006.01) |
| *C07K 16/28* | (2006.01) |
| *G01N 33/68* | (2006.01) |
| *A61K 38/17* | (2006.01) |
| *A61K 45/06* | (2006.01) |
| *A61K 39/395* | (2006.01) |

(52) U.S. Cl.
CPC ....... *C07K 14/70578* (2013.01); *A61K 38/177* (2013.01); *A61K 39/3955* (2013.01); *A61K 45/06* (2013.01); *C07K 14/70575* (2013.01); *C07K 16/2875* (2013.01); *C07K 16/2878* (2013.01); *G01N 33/6863* (2013.01); *C07K 2319/30* (2013.01); *C07K 2319/32* (2013.01); *G01N 2333/70575* (2013.01); *G01N 2800/22* (2013.01)

(58) Field of Classification Search
None
See application file for complete search history.

(56) References Cited

U.S. PATENT DOCUMENTS

2003/0170244 A1* 9/2003 Pluenneke ............. A61K 35/17
424/146.1

FOREIGN PATENT DOCUMENTS

| WO | 2004085478 A3 | 10/2004 |
|---|---|---|
| WO | 2006055302 A3 | 5/2006 |

OTHER PUBLICATIONS

Boula et al. Effect of cA2 Anti-Tumor Necrosis Factor-alpha Antibody Therapy on Hematopoiesis of Patients with Myelodysplastic Syndromes. Clin Cancer Research vol. 12(10):3099-3108 (May 15, 2006).*
Deeg et al. Soluble TNF receptor fusion protein (TNFR:Fc;Enbrel) in the treatment of patients with myelodysplastic syndrome (MDS). Blood, Abstract. vol. 96, No. 11 Part 1, pp. 146a. print (Nov. 16, 2000).*
Gupta et al. Fas ligand expression in the bone marrow in myelodysplastic syndromes correlates with FAB subtype and anemia, and predicts survival. Leukemia vol. 13, 44-53 (1999).*
Gersuk et al. A role for tumour necrosis factor-a, Fas and Fas-Ligand in marrow failure associated with myelodysplastic syndrome. British Journal of Haematology, vol. 103, 176-188 (1998).*
Komeno et al. Molecular Bases of Myelodysplastic Syndromes: Lessons from Animal Models. J. Cell. Physiol. 219: 529-534, (2009).*
Tokuriki et al., Stability effects of mutations and protein evolvability; Current Opinion in Structural Biology, 19:596-604 (2009).*
Wells, Additivity of Mutational Effects in Proteins. Biochemistry 29:8509-8517 (1990).*
Schmidt-Mende et al. Granulocyte colony-stimulating factor inhibits Fas-triggered apoptosis in bone marrow cells isolated from patients with refractory anemia with ringed sideroblasts Leukemia vol. 15, 742-751 (2001).*
Tehranchi et al. Granulocyte colony-stimulating factor inhibits spontaneous cytochrome c release and mitochondria-dependent apoptosis of myelodysplastic syndrome hematopoietic progenitors Blood vol. 101/3:1080-1086 (Feb. 1, 2003).*
Geoffrey M. Gersuk et al: "A role for tumour necrosis factor-alpha, Fas and Fas-Ligand in marrow failure associated with myelodysplatic syndrome". British Journal of Haematology. vol. 103. No. 1. Oct. 1, 1998 (Oct. 1, 1998). pp. 176-188. XP55075352. ISSN: 0007-1048. DOI: 10.1046/j.1365-2141.1998.00933.x abstract page 185. right hand column—p. 186. right hand column.
P. Gupta et al: "Fas ligand expression in the bone marrow in myelodysplastic syndromes correlates with FAB subtype and anemia. and predicts survival", Leukemia.vol. 13. No. 1. Jan. 1, 1999 (Jan. 1, 1999). pp. 44-53. XP55075351. ISSN: 0887-6924. DOI: 10.1038/sj.leu.2401233 abstract p. 51.
Miller: "Myelodysplastic syndroms", Current Treatment Options in Ongology. vol. 1. No. 1. Apr. 1, 2000 (Apr. 1, 2000). pp. 63-69. XP55075646. ISSN: 1527-2729 the whole document.
Li, Da-Qi et al: "Expression of Fas(CD95) and fas ligand in the marrow of patients with myelodysplastic syndromes and their effects on progenitor cells", Acta Academiae Medicinae Shanghai. Shanghai. CN. vol. 29. No. 4. Jul. 1, 2002 (Jul. 1, 2002). pp. 276-279. XP009171907, English Abstract.

(Continued)

*Primary Examiner* — Elizabeth C Kemmerer
*Assistant Examiner* — Regina M Deberry
(74) *Attorney, Agent, or Firm* — Perkins Coie LLP; Viola T. Kung

(57) ABSTRACT

The present invention relates to inhibitors of the CD95 signaling pathway for the use in the treatment of Myelodysplastic Syndrom (MDS) wherein the MDS is selected from the IPSS low risk MDS subgroup and/or the IPSS intermediate-1 (int-1) risk MDS subgroup as well as a method for the diagnosis of MDS.

8 Claims, 14 Drawing Sheets

(56) References Cited

OTHER PUBLICATIONS

Gersuk, G. M. et al: "A role for Fas. Fas-ligand and TNF-alpha in the dysregulation of hematopoiesis in myelodysplastic syndrome (MOS)", Blood; Thirty-Eighth Annual Meeting of the American Society of Hematology. American Society of Hematology. US; Orlando. Florida. USA. vol. 88. No. 10 Suppl.1 Part 1-2. Dec. 1, 1996 (Dec. 1, 1996). p. 639A. XP009171909, Abstract.

* cited by examiner

SEQUENCE LISTING

```
<160> NUMBER OF SEQ ID NOS: 1

<210> SEQ ID NO 1
<211> LENGTH: 400
<212> TYPE: PRT
<213> ORGANISM: Artificial Sequence
<220> FEATURE:
<223> OTHER INFORMATION: Recombinant fusion protein consisting of human
      CD95 extracellular domain with human IgG1 FC-part to its
      C-terminus
<220> FEATURE:
<221> NAME/KEY: SIGNAL
<222> LOCATION: (1)..(16)
<223> OTHER INFORMATION: Variable cleavage sites
<220> FEATURE:
<221> NAME/KEY: SIGNAL
<222> LOCATION: (1)..(20)
<223> OTHER INFORMATION: Variable cleavage sites
<220> FEATURE:
<221> NAME/KEY: SIGNAL
<222> LOCATION: (1)..(25)
<223> OTHER INFORMATION: Variable cleavage sites
<220> FEATURE:
<221> NAME/KEY: DOMAIN
<222> LOCATION: (26)..(172)
<223> OTHER INFORMATION: Human CD95 extracellular domain
<220> FEATURE:
```

```
<221> NAME/KEY: MOD_RES
<222> LOCATION: (26)..(26)
<223> OTHER INFORMATION: PYRROLIDONE CARBOXYLIC ACID
<220> FEATURE:
<221> NAME/KEY: DISULFID
<222> LOCATION: (59)..(73)
<220> FEATURE:
<221> NAME/KEY: DISULFID
<222> LOCATION: (63)..(82)
<220> FEATURE:
<221> NAME/KEY: DISULFID
<222> LOCATION: (85)..(101)
<220> FEATURE:
<221> NAME/KEY: DISULFID
<222> LOCATION: (104)..(119)
<220> FEATURE:
<221> NAME/KEY: DISULFID
<222> LOCATION: (107)..(127)
<220> FEATURE:
<221> NAME/KEY: CARBOHYD
<222> LOCATION: (118)..(118)
<223> OTHER INFORMATION: N-linked Glycosylation at Position N118
<220> FEATURE:
<221> NAME/KEY: DISULFID
<222> LOCATION: (129)..(143)
<220> FEATURE:
<221> NAME/KEY: DISULFID
<222> LOCATION: (135)..(140)
<220> FEATURE:
<221> NAME/KEY: CARBOHYD
<222> LOCATION: (136)..(136)
<223> OTHER INFORMATION: N-linked Glycosylation at Position N136
<220> FEATURE:
<221> NAME/KEY: DISULFID
<222> LOCATION: (146)..(157)
<220> FEATURE:
<221> NAME/KEY: DISULFID
<222> LOCATION: (149)..(165)
<220> FEATURE:
<221> NAME/KEY: DOMAIN
<222> LOCATION: (172)..(400)
<223> OTHER INFORMATION: Human IgG1-FC domain
<220> FEATURE:
<221> NAME/KEY: DISULFID
<222> LOCATION: (173)..(173)
<223> OTHER INFORMATION: Interchain cystine forming residue of the
      APG101 homodimer.
<220> FEATURE:
<221> NAME/KEY: DISULFID
<222> LOCATION: (179)..(179)
<223> OTHER INFORMATION: Interchain cystine forming residue of the
      APG101 homodimer.
<220> FEATURE:
<221> NAME/KEY: DISULFID
<222> LOCATION: (182)..(182)
<223> OTHER INFORMATION: Interchain cystine forming residue of the
      APG101 homodimer.
<220> FEATURE:
<221> NAME/KEY: DISULFID
<222> LOCATION: (214)..(274)
<220> FEATURE:
<221> NAME/KEY: CARBOHYD
<222> LOCATION: (250)..(250)
<223> OTHER INFORMATION: N-linked Glycosylation at Position N250
<220> FEATURE:
<221> NAME/KEY: DISULFID
<222> LOCATION: (320)..(378)

<400> SEQUENCE: 1

Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
            35                  40                  45
```

```
Leu Glu Gly Leu His His Asp Gly Gln Phe Cys His Lys Pro Cys Pro
    50              55                  60

Pro Gly Glu Arg Lys Ala Arg Asp Cys Thr Val Asn Gly Asp Glu Pro
65              70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
        130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Cys Asp Lys Thr
                165                 170                 175

His Thr Cys Pro Pro Cys Pro Ala Pro Glu Leu Leu Gly Gly Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
            245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
        275                 280                 285

Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
            325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
            355                 360                 365

Arg Trp Gln Gln Gly Asn Val Phe Ser Cys Ser Val Met His Glu Ala
    370                 375                 380

Leu His Asn His Tyr Thr Gln Lys Ser Leu Ser Leu Ser Pro Gly Lys
385                 390                 395                 400
```

INHIBITORS OF THE CD95 SIGNALING PATHWAY FOR TREATMENT OF MDS

CROSS REFERENCE TO RELATED APPLICATION

This application is a 35 U.S.C. 371 National Phase Entry Application from PCT/EP2013/065245, filed Jul. 18, 2013, which claims the benefit of European Patent Application No. 12176974.9 filed on Jul. 18, 2012, the disclosure of which is incorporated herein in its entirety by reference.

The present invention relates to inhibitors of the CD95 signaling pathway for the use in the treatment of Myelodysplastic Syndrom (MDS) wherein the MDS is selected from the IPSS low risk MDS subgroup and/or the IPSS intermediate-1 (int-1) risk MDS subgroup as well as a method for the diagnosis of MDS.

Myelodysplastic syndromes (MDS) are clonal hematopoietic stem cell disorders characterized by ineffective hematopoiesis leading to blood cytopenias, especially anemia, and often evolving to acute myeloid leukemia (AML). In particular, MDS may be characterized by defective erythroid progenitor growth. Correspondingly, MDS are commonly classified based on morphology and blast cell percentage in blood and bone marrow (French American British (FAB) and WHO classifications) (Bennett et al, 1982; Vardiman et al, 2009).

Figure 1:
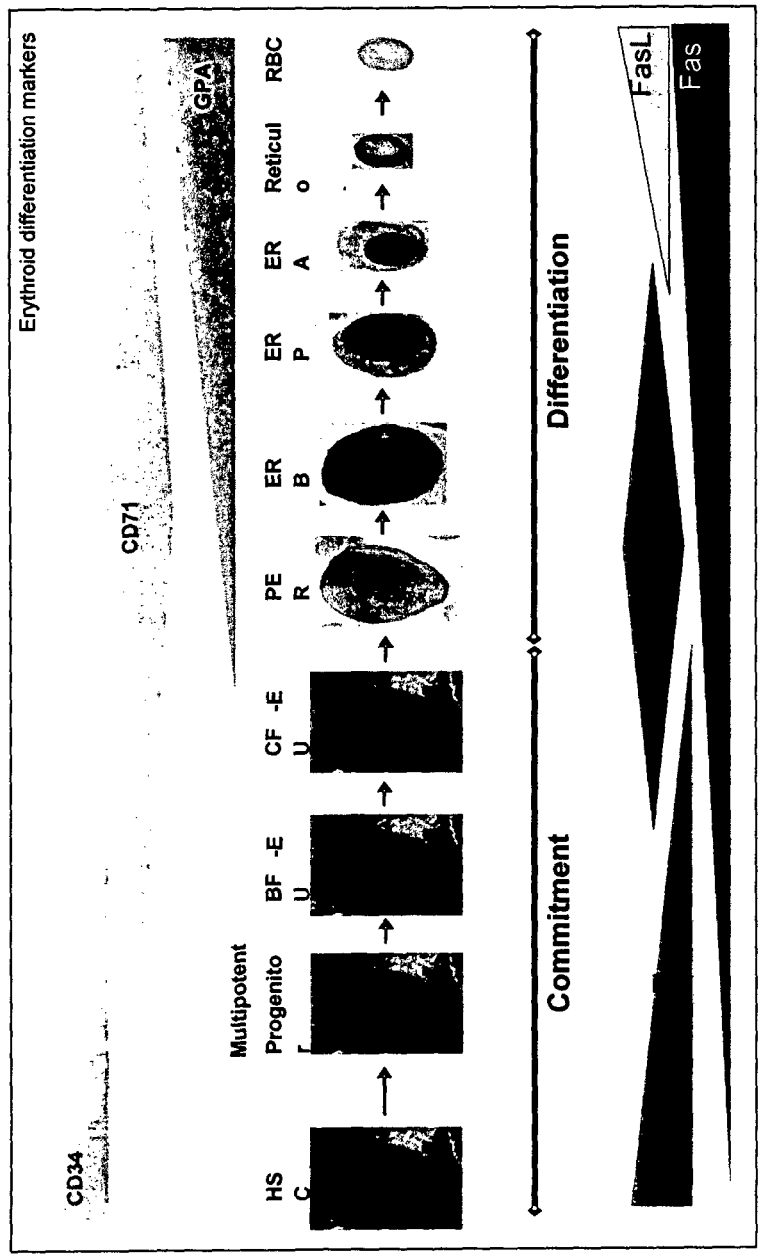

Erythropoiesis is controlled by a balance between positive and negative signals that implicate cell-cell interaction and soluble factors in the bone marrow erythroblastic islands. An overview on erythropoiesis is shown in FIG. 1. Commitment of the CD34$^+$ hematopoietic stem cell (HSC) to the erythroid lineage is under the control of important transcription factor like GATA-1 and cytokines like the c-Kit ligand, stem cell factor (SCF). The size of the erythroid compartment is upregulated by erythropoietin that stimulates the maturation of CFU-E and pro-erythroblasts and prevents their apoptosis. Erythroid cells acquire membrane CD71 (transferring receptor) expression followed by the glycophorin A (GPA) on the more mature cells (FIG. 1).

The negative regulation of erythropoiesis depends on Fas/FasL that contributes to the apoptosis of immature erythroblasts that express Fas by interaction with FasL that is expressed on mature erythroid precursors (De Maria et al, 1999) and also by autoregulation of erythroblasts at the same stage of differentiation (Socolovski et al, 2008). The maturation of normal erythroid precursors requires the activation of caspase-3, although caspase-8 activity is not evidenced (De Maria et al, 1999; Zermati et al, 2001) Cleavage of caspase-3 substrates is limited. For instance, GATA-1 is a substrate for caspase-3 in conditions of erythropoietin deprivation, although in the presence of Epo, GATA-1 is protected from cleavage by interaction with Hsp70 that translocates from the cytosol to the nucleus (Ribeil et al, 2007).

MDS dyserythropoiesis is associated with ectopic activation of caspase-8 downstream of Fas. The applicant's group and others have previously demonstrated that Fas is overexpressed at the surface of CD34+ immature progenitors and in erythroid committed progenitors. Fas expression increased along erythroid differentiation with the onset of Fas ligand expression in GPA-positive erythroid precursors resulting in ectopic activation of caspase-8 in the erythroid lineage. This was observed in fresh bone marrow cells (Bouscary et al, 1997) as well as in erythroid cells derived in a 2-step liquid culture (Claessens et al, 2002). Inhibition of Fas signalling by ectopic expression of a lentivirally expressed dominant negative mutant of the adaptor FADD, decreased caspase-8 activation, and inhibited apoptosis in MDS erythroid precursors (Claessens et al, 2005). Fas/FasL may contribute to prevent normal erythroid differentiation and induce apoptosis in MDS erythroid cells.

Recent data demonstrated that erythroid cell maturation is severely impaired in low grade MDS. The erythroid cell precursors were quantified by CD71/GPA labelling described by Socolovski et al (2007). It was observed that the fraction of CD71$^{high}$/GPA$^{low}$ cells is increased and CD71$^{int}$/GPA$^{high}$ is decreased in MDS cell cultures compared to normal cultures after 7 days. Transcriptomic studies of day-14 erythroid precursors demonstrated a 2-fold decreased expression of GYPA encoding the glycophorin A (GPA). In addition, several other erythroid genes were downregulated.

MDS are rare diseases (incidence 3 to 5/100 000 persons/year) and predominate in the elderly (median age 65 to 70 years).

Commonly MDS is treated by the administration of classical erythropoiesis stimulating agents (ESAs).

However, until the present invention MDS patients which are resistant to ESAs were difficult to treat.

Thus, it was the object of the present invention to provide a new treatment option for MDS, in particular for the treatment of MDS patients which are resistant to ESA.

A first aspect of the invention relates to an inhibitor of the CD95 signalling pathway for use in the treatment of myelodysplastic syndrome (MDS), which is selected from the IPSS low-risk MDS subgroup and/or the IPSS intermediate (int-1 risk MDS subgroup).

According to the invention the terms CD95, CD95R and CD95-receptor may be used interchangeable. Further synonyms are Apo-1 or Fas which may be used interchangeable herein. Further, the terms CD95L, CD95-ligand and the corresponding synonyms FasL, Apo-1L, CD178 or TNF-SF6 may be used interchangeable.

An "inhibitor of the CD95 signalling pathway" in terms of the present invention may be any compound which interferes or blocks at least partially the CD95 signalling pathway. According to a preferred embodiment an "inhibitor of the CD95 signalling pathway" blocks the CD95 signalling pathway. Methods for determining and/or assessing CD95 signal pathway activity are known to the person skilled in the art and are, for example, described by Lavrik et. al. (*Cell Death Differ.* 2012 Jan.; 19(1):36-41 Regulation of CD95/Fas signaling at the DISC).

An inhibitor according to the invention may act on the protein level and/or the nucleic acid level. Inhibitors acting on the protein level may be selected from antibodies, proteins and/or small molecules. Inhibitors acting on the nucleic acid level are for example antisense molecules, RNAi molecules and/or ribozymes.

According to an especially preferred embodiment the inhibitor binds to the CD95 receptor (CD95) and/or the CD95 ligand (CD95L). In a further embodiment, the CD95/CD95L interaction may be inhibited.

In one preferred embodiment, the inhibitor according to the invention is an antibody or a functional fragment thereof. The inhibitor being an antibody may bind to CD95, but, of course, also to CD95L. An example for an antibody binding CD95L is Nok-1.

The antibody may be, for example, a monoclonal antibody, a polyclonal antibody, a recombinant antibody, a humanized antibody, a human antibody, a chimeric antibody, a multi-specific antibody, or an antibody fragment thereof (e.g., a Fab fragment, a Fab' fragment, a F(ab')2 fragment, a Fv fragment, a diabody, or a single chain antibody molecule). The antibody can be of the IgG1-, IgG2-, IgG3- or IgG4-type.

The antibody may be used with or without modification, and may be labelled, either covalently or non-covalently, with, for example, a reporter group or a effector group.

An "antibody fragment" according to the invention presents essentially same epitope binding site as the corresponding antibody does and/or has substantially the same CD95 and/or CD95L inhibiting activity as the corresponding antibody has.

Methods for producing antibodies of the invention are known to the person skilled in the art.

One kind of inhibitor encompassed by the present invention may be a CD95-ligand inhibitor. For example, CD95-ligand inhibitors may be selected from (a) an inhibitory anti-CD95 ligand-antibody or a fragment thereof as outlined above; (b) a soluble CD95 receptor molecule or a CD95 ligand-binding portion thereof; and (c) a CD95-ligand inhibitor selected from FLINT, DcR3 or fragments thereof.

Soluble CD95 receptor molecules, e.g. a soluble CD95 receptor molecule without transmembrane domain are described in EP-A-0 595 659 and EP-A-0 965 637 or CD95 receptor peptides as described in WO 99/65935

The Fas ligand inhibitor FLINT or DcR3 or a fragment, e.g. soluble fragment thereof, for example the extracellular domain optionally fused to a heterologous polypeptide, particularly a Fc immunoglobulin molecule is described in WO 99/14330 or WO 99/50413. FLINT and DcR3 are proteins which are capable of binding the CD95 ligand.

In a further embodiment the inhibitor is a fusion protein, in particular a fusion protein that binds to a CD95L.

In one embodiment, a CD95L inhibitor comprises an extracellular domain of the CD95R molecule, such as amino acids 1 to 172 (MLG . . . SRS) of the mature CD95 sequence according to U.S. Pat. No. 5,891,434. This extracellular domain of the CD95R molecule may be fused to a heterologous polypeptide domain, particularly a Fc immunoglobulin molecule including the hinge region e.g. from the human IgG1 molecule. A fusion protein comprising an extracellular CD95 domain and a human Fc domain is described in WO 95/27735.

Thus, according to a preferred embodiment, the agent which binds to CD95L is a fusion protein comprising an extracellular CD95 domain and a Fc domain, in particular a human Fc domain.

According to an especially preferred embodiment, the agent that binds to CD95L is APG101 or functional fragments, isoforms and/or derivatives thereof. APG101 comprises the domains CD95R (amino acids 26-172; ECD extracellular domain) and IgG1-Fc (amino acids 172-400) of SEQ ID NO:1). APG101 and derivatives thereof are disclosed in WO95/27735 and WO2004/085478.

In still a further embodiment of the present invention the inhibitor is a nucleic acid effector molecule. The nucleic acid effector molecule may be DNA; RNA, PNA or an DNA-RNA-hybrid. It may be single stranded or double stranded. Expression vectors derived from retroviruses, adenovirus, herpes or vaccina viruses or from various bacterial plasmids may be used for delivery of nucleotide sequences to the targeted organ, tissue or cell population. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

The nucleic acid effector molecule may be in particular selected from antisense molecules, RNAi molecules and ribozymes which are preferably capable of inhibiting the expression of the CD95R and/or CD95L gene. As outlined above, the present invention relates in particular to the treatment of Myelodysplastic Syndrom (MDS) which is selected from the International Prognostic Scoring System (IPSS) low risk MDS subgroup and/or the IPSS intermediate-1 (int-1) risk MDS subgroup.

The IPSS is well known to the person skilled in the art. Main prognostic factors of MDS for progression to AML and survival include the number and importance of cytopenias, the percent of marrow blasts and the bone marrow cytogenetic abnormalities. Each indicator is rated according to its severity and the ratings are combined into a "score", the IPSS.

The IPSS distinguishes 4 subgroups with significantly different risk of progression to AML and survival: low, intermediate-1 (int-1), intermediate-2 (int-2) and high risk. Low and int-1 risk subgroups are often grouped together as <<favourable>> or low-risk MDS, and int-2 and high risk subgroups are <<unfavourable>> or high-risk MDS (Greenberg et al, 1997).

Low-risk MDS (with low or int-1 IPSS) are characterized by increased apoptosis of marrow progenitors that lead to a large extent to cytopenias. In most patients, erythroid cell show impaired differentiation and increased apoptosis.

Thus, a MDS subgroup to be treated according to the present invention, i.e. with low risk or int-1 IPSS may be characterised by increased apoptosis during erythropoiesis.

According to a further embodiment, a MDS subgroup to be treated may be further characterised by a severe defect of erythropoiesis without excess of blast.

Another characterising feature a MDS subgroup to be treated may be resistance to classical erythropoiesis stimulating agents (ESA) and/or colony stimulating factors. An erythropoiesis stimulating agent according to the invention may be any compound which stimulates red blood cell production. Examples for an ESA and/or colony stimulating factors comprise but are not limited to Erythropoietin (Epo), Epoetin alpha (Procrit/Epogen), Epoetin beta (NeoRecormon), Darbepoetin alfa (Aranesp), Methoxy polyethylene glycol-epoetin beta (Mircera) and or some cytokines such IL-3 or Il-9.

The MDS subgroup to be treated may be characterised by a low burst forming unit-erythroid (BFU-E) value and/or a low colony-forming unit-erythroid (CFU-E) value.

Of course the characteristics discussed above may be combined in any possible combination to describe a MDS subgroup to be treated.

Having a MDS subgroup as described above in mind, a further embodiment of the invention relates to the use of inhibitors which increase the number of BFU-E and not affect colony-forming-unit-granulocyte monocytes (CFU-GM) and/or without increasing the risk of leukemic cell expansion. Preferably, the inhibitor may be also compound which improves the growth of erythroid progenitors.

An inhibitor of the CD95 signalling pathway used according to the present invention course may be provided as a pharmaceutical composition. This composition may comprise pharmaceutically acceptable carriers, diluents and/or adjuvants, etc.

Further details on techniques for formulation and administration may be found in the latest edition of Remington's Pharmaceutical Sciences (Maack Publishing Co., Easton, Pa.).

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means.

Pharmaceutical compositions suitable for use in the invention include compositions wherein the active ingredients are contained in an effective amount to achieve the intended purpose. The determination of an effective dose is well within the capability of those skilled in the art. A therapeutically effective dose refers to that amount of active ingredient, for example a nucleic acid or a protein of the invention or an antibody, which is sufficient for treating a specific condition. The exact dosage will be determined by the practitioner, in light of factors related to the subject that requires treatment.

Dosage and administration are adjusted to provide sufficient levels of the active moiety or to maintain the desired effect. A person skilled in the art is aware of further methods to provide sufficient levels of the active moiety and/or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. In a preferred embodiment the total amount of the inhibitor of the CD95 signalling pathway according to the present invention to be administered for a patient suffering from MDS is from about 50 to about 400 mg/week, more preferably about 100 to about 200 mg/week. The preferred weekly dose can be administered as a single dose or as several doses. Especially preferred is a single dose particularly from 100 to 200 mg/week which is administered intravenously as a single dose.

The treatment can last for several weeks. In each individual case, the duration of the treatment is determined by the supervising doctor and is e.g. based on the success of the treatment, the occurance of side effects etc.

According to a further aspect of the present invention this pharmaceutical composition may comprise at least one further active ingredient such as an agent commonly used for the treatment of MDS, such as 5-azacitidine, decitabine or Lenalidomide, an erythropoiesis-stimulating agent and/or an apoptosis-inhibiting agent.

Examples for erythropoiesis-stimulating agents have been specified above.

Examples for apoptosis-inhibiting agents comprise caspase inhibitors such as xIAP, c-IAP-1, c-IAP2, Survivin, TNF-α-inhibiting compounds such as Revlimid, Pomalidomide, Bcl-2 family protein inhibitors etc.

A further aspect of the present invention is a pharmaceutical composition comprising an inhibitor in terms of the present invention, further comprising an erythropoiesis-stimulating agent, in particular an erythropoiesis-stimulating agent as defined above.

A further aspect of the invention relates to a method for the diagnosis of MDS, comprising the step determining CD95 expression in a sample, wherein CD95L overexpression is predictive of the disease. A further step of this inventive method might be inter alia the comparison of the determined CD95L expression value with a control value such as from a sample of a patient with anemia of other origin than MDS.

Of course, the inventive diagnosis method can be combined with known methods such as the IPSS system.

FIGURE LEGENDS

FIG. 1: Overview of erythropoiesis. HSC: hematopoietic stem cell. BFU-E: burst forming unit-erythroid, CFU-E: colony forming unit-erythroid, PER: proerythroblast, ERB: basophilic erythroblast, ERP: polychromatophilic erythroblast, ERA: acidophilic erythroblast, reticulo: reticulocyte, RBC: red blood cell, SCF: stem cell factor, EPO: erythropoietin.

Figure 2:
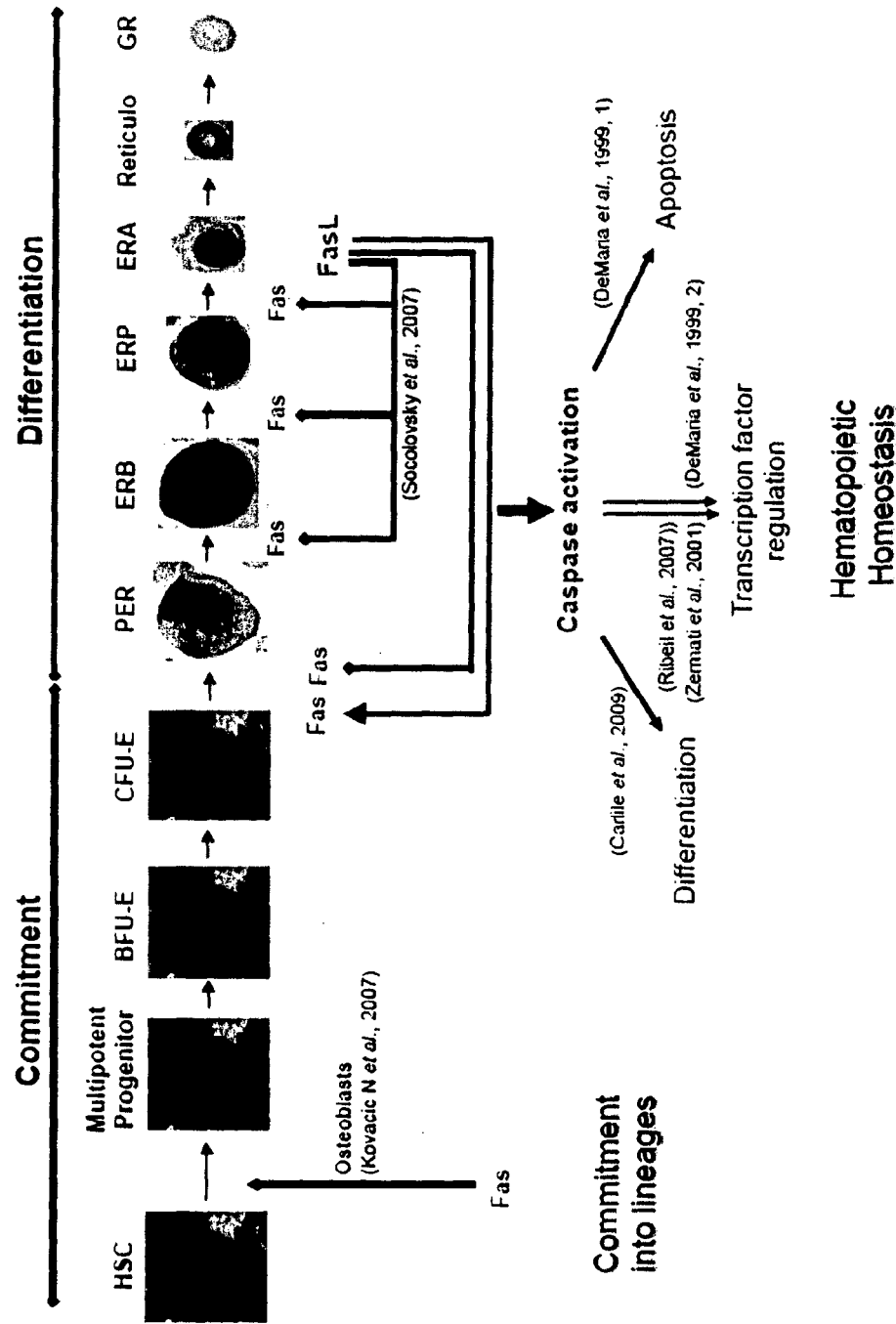

FIG. 2: Negative regulation of normal and MDS erythropoiesis. Normal erythropoiesis is controlled by a negative regulation of proliferation through Fas-dependent apoptosis of immature progenitors mediated by FasL-expressing mature cells (blue arrows). In MDS, Fas and FasL are overexpressed leading to excessive and inappropriate apoptosis (red arrows).

Figure 3:
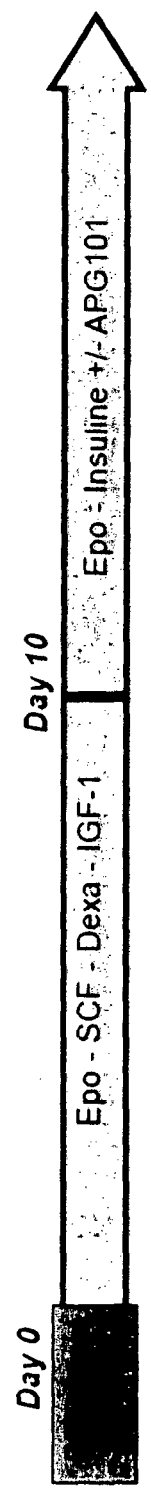

FIG. 3: Role/Concentration of Fas and FasL during erythropoiesis.

Figure 4:
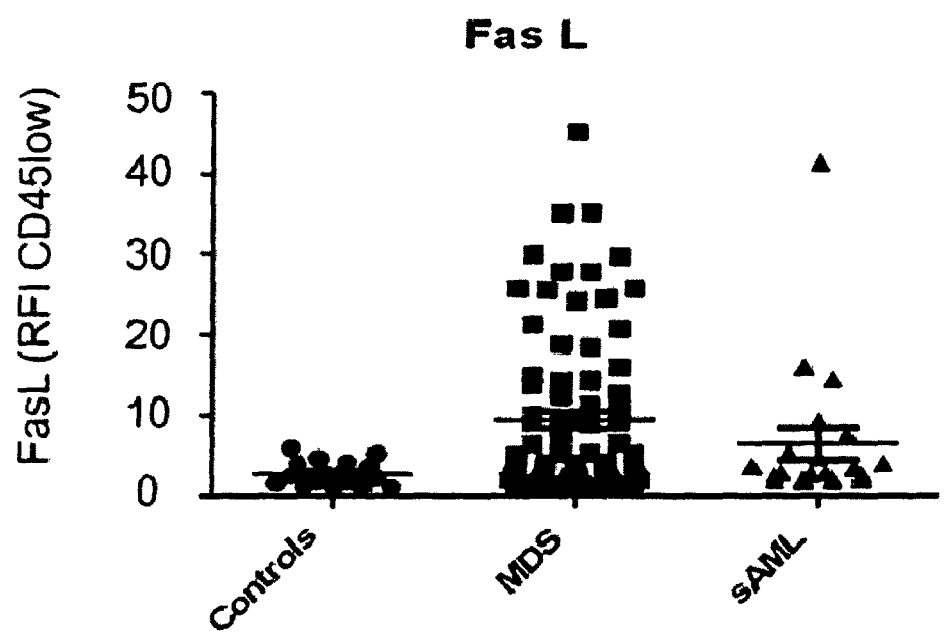
Figure 4:
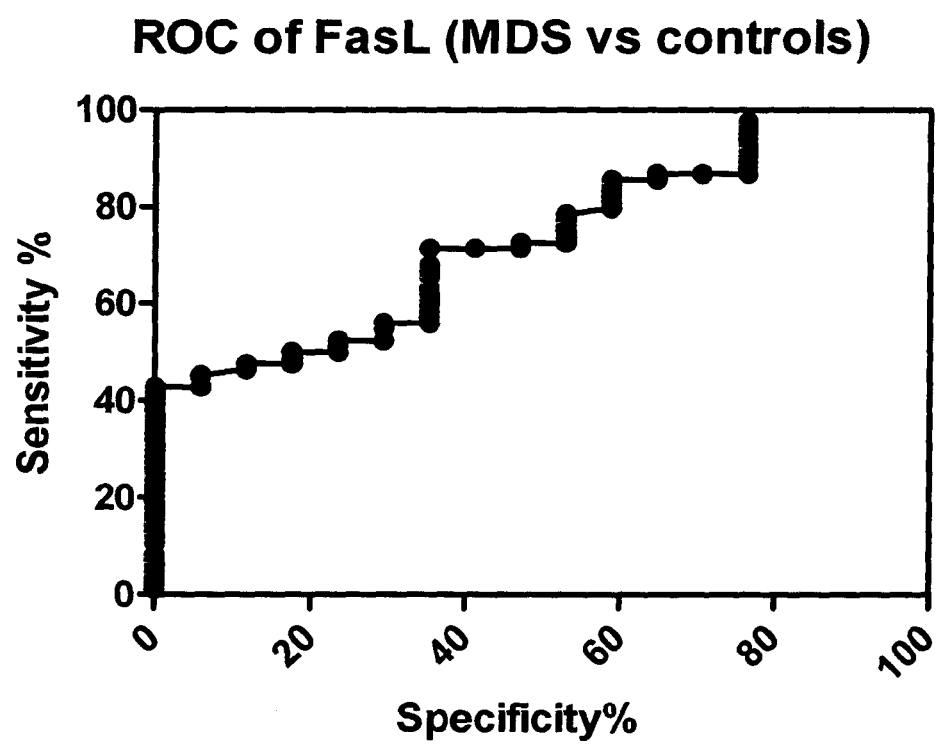

FIG. 4: FasL expression in MDS, sAML and controls. A. Distribution of FasL RFI. B. ROC analysis comparing MDS to controls.

Figure 5:
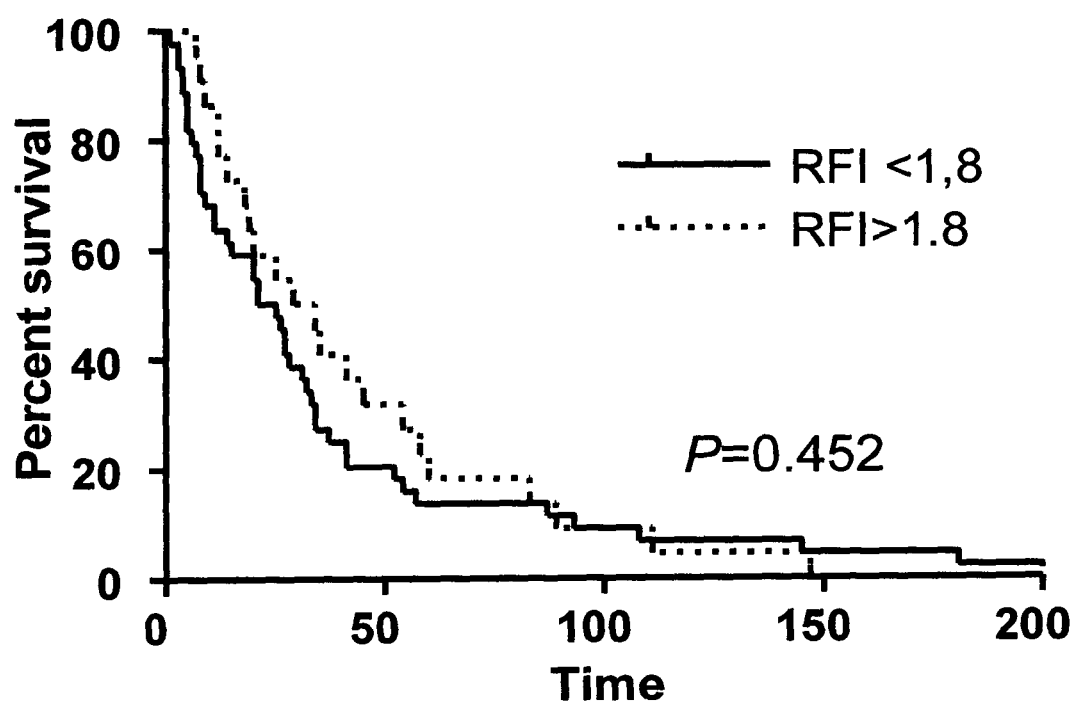

FIG. 5: Impact of Fas expression on $CD45^{lo}/CD34^+$ cells at diagnosis on overall survival.

Figure 6:
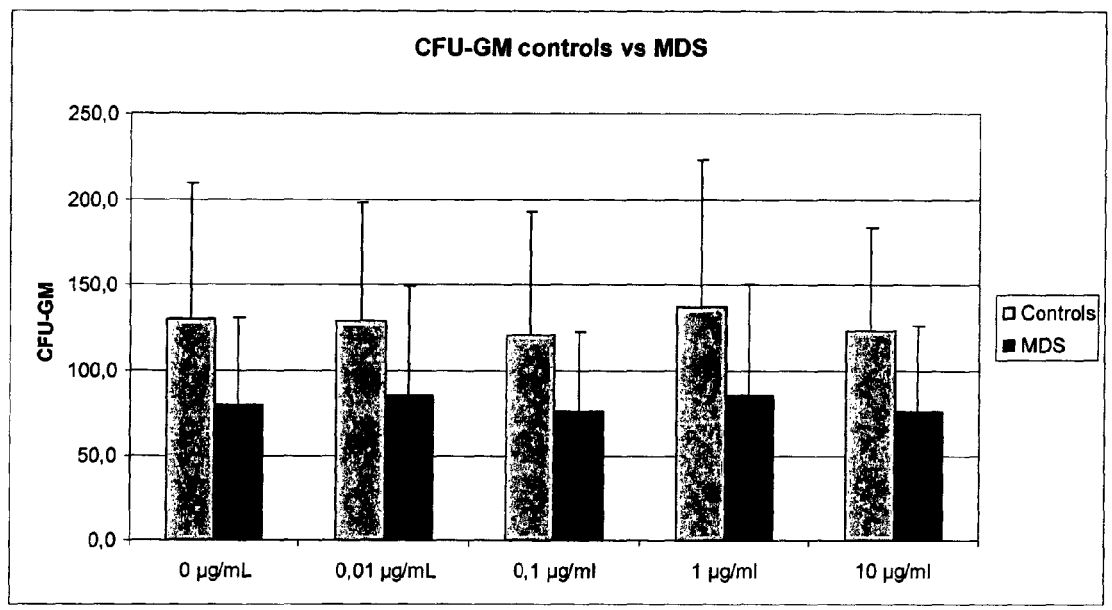
Figure 6:
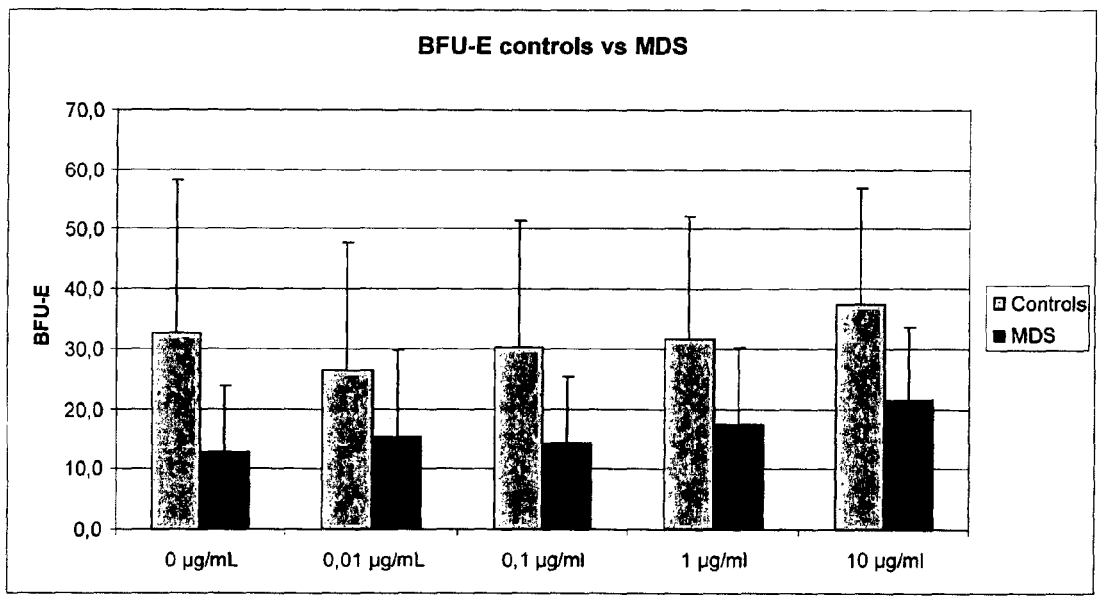

FIG. 6: Effect of APG101 on BFU-E and CFU-GM growth at day 14 of the methylcellulose culture.

Figure 7:
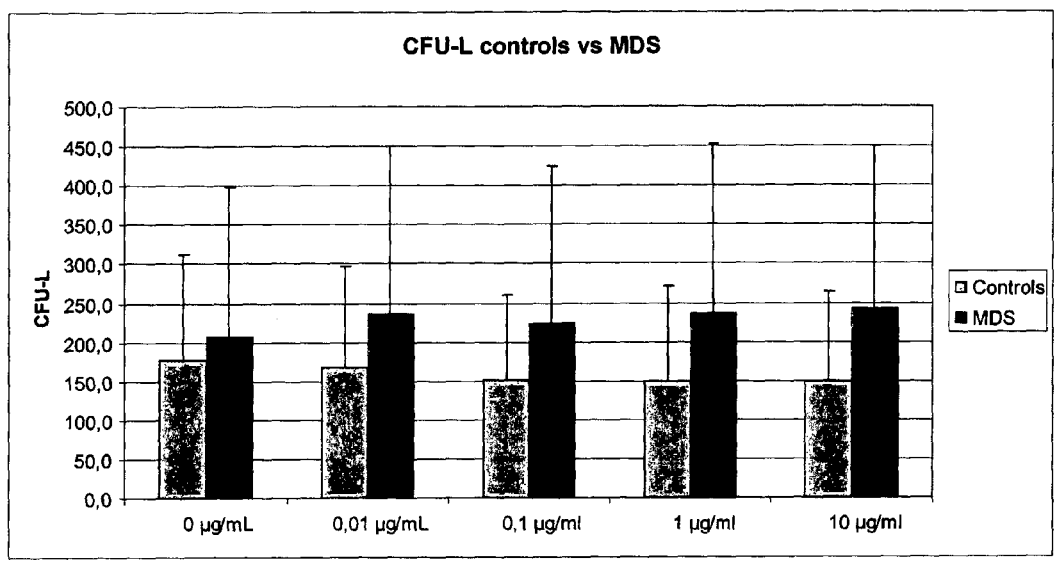
Figure 7:
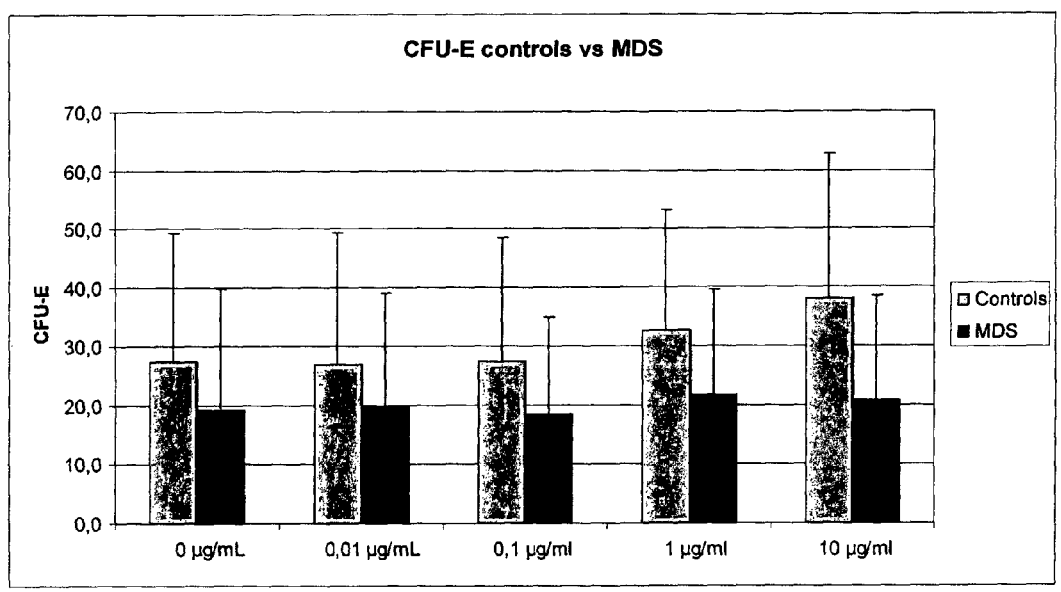

FIG. 7: Effect of APG101 on CFU-E and CFU-L growth at day 7 of the methylcellulose culture.

Figure 8:
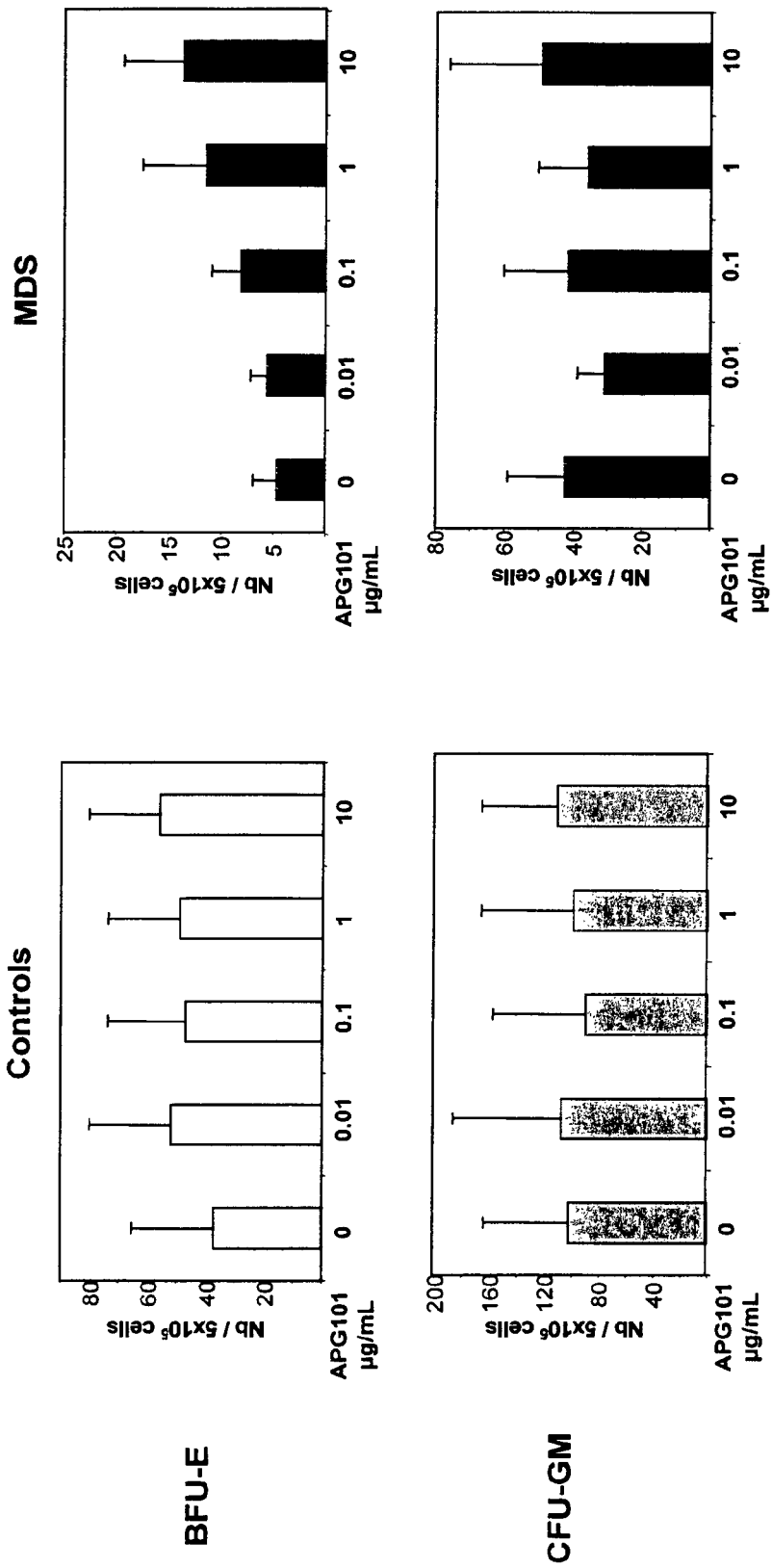

FIG. 8: Effect of APG101 on BFU-E and CFU-GM deriving from liquid cultures at day 5.

Figure 9:
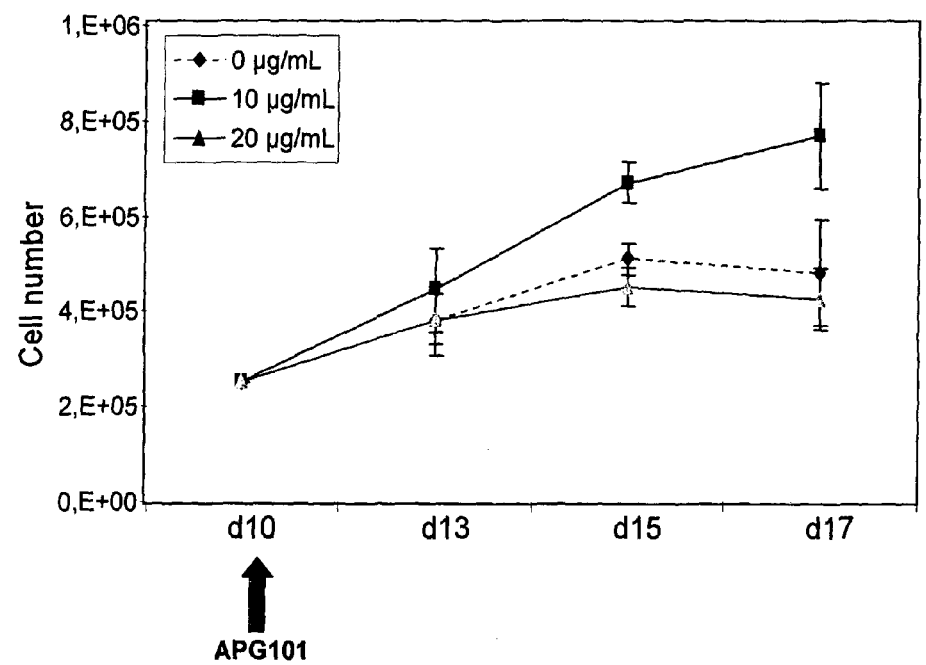
Figure 9:
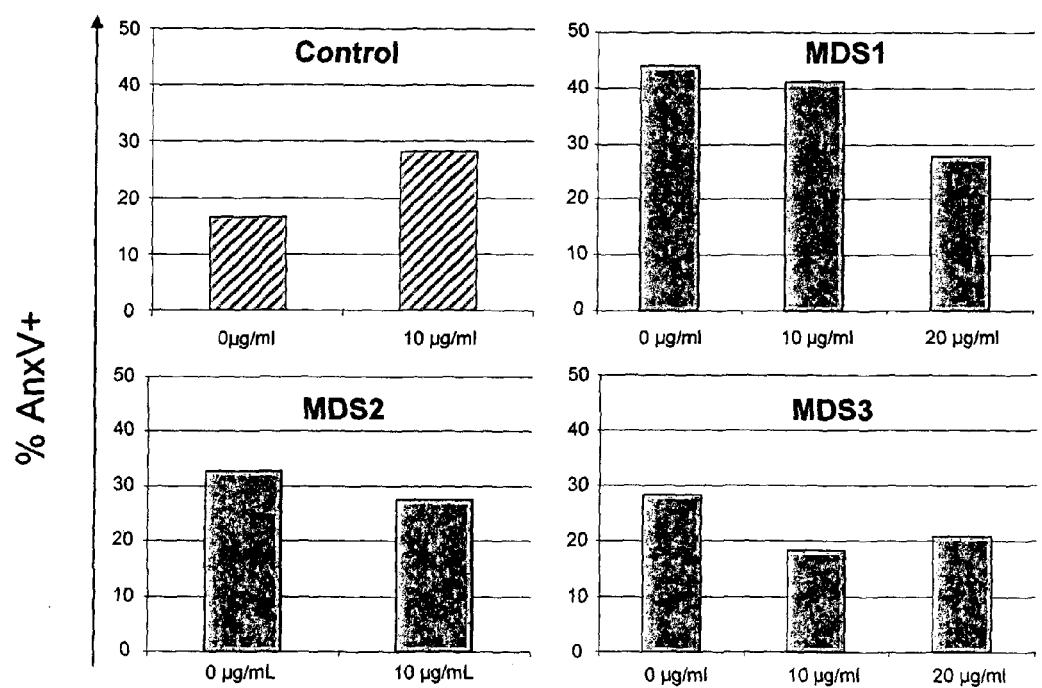

FIG. 9: Effect of APG101 added at the differentiation phase in liquid culture of erythroid progenitors.

Figure 10:
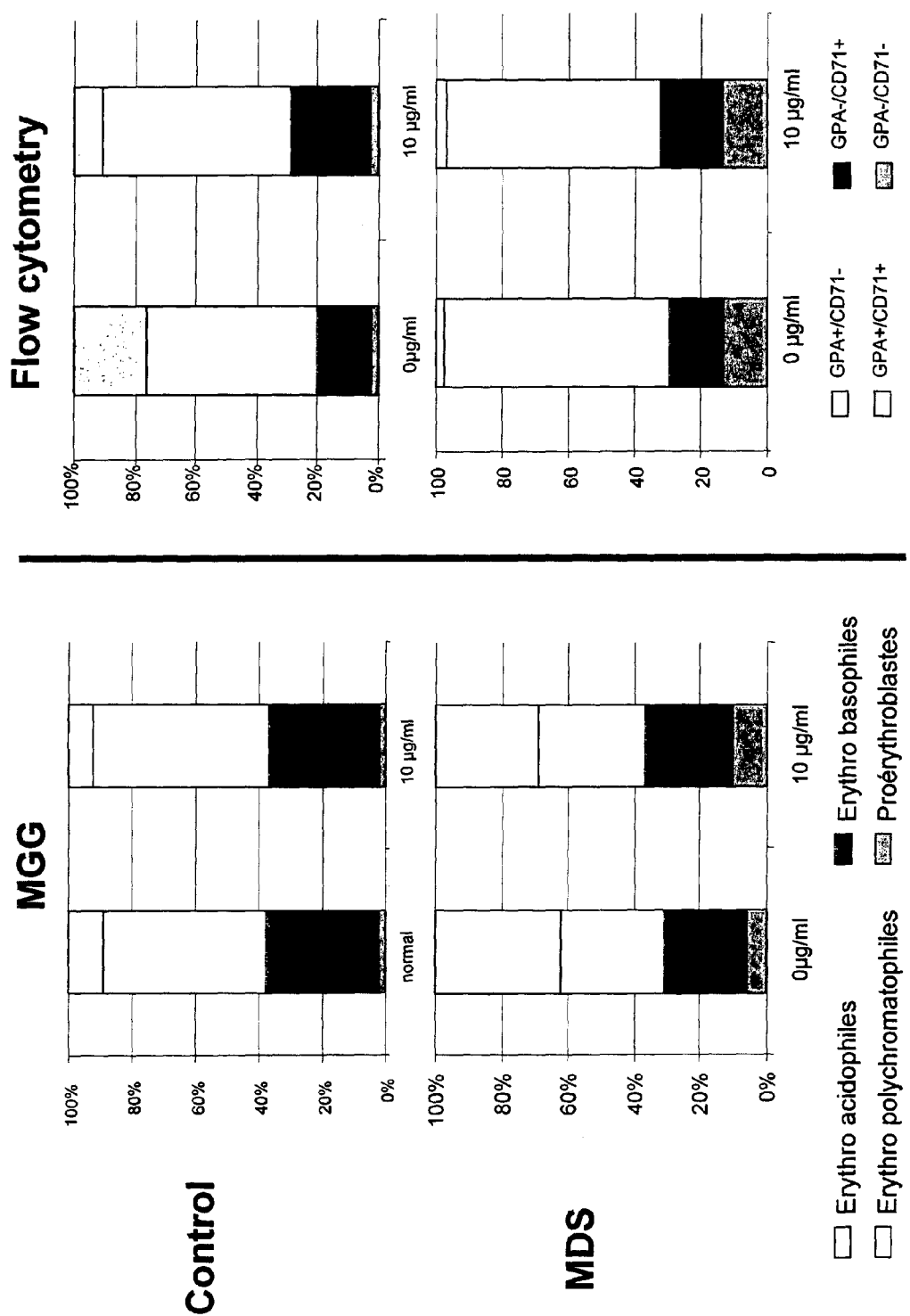

FIG. 10: Effect of APG101 on erythroid cell differentiation. Left: MGG coloured cytospins. Right: Flow cytometry analysis of CD71/GPA double labelling.

Figure 11:
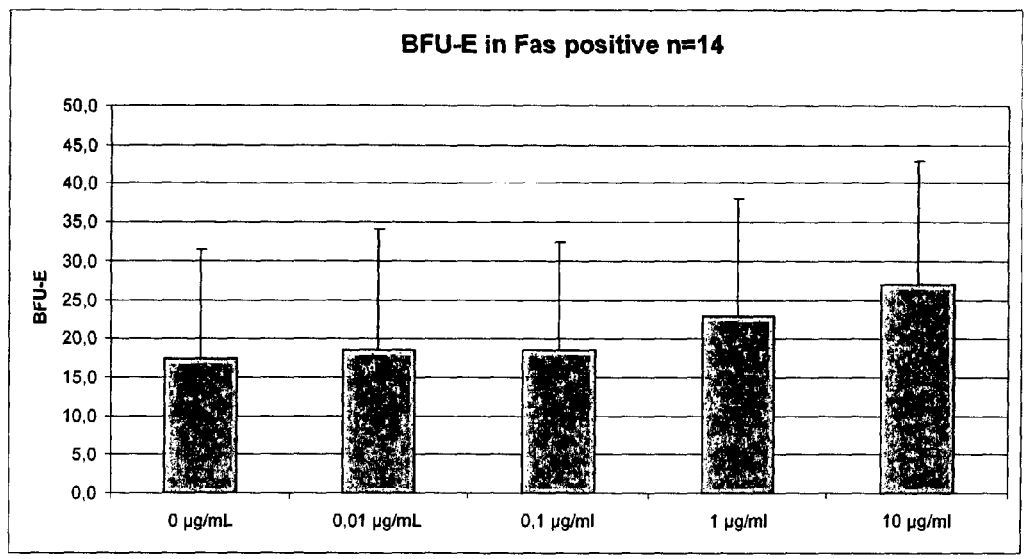
Figure 11:
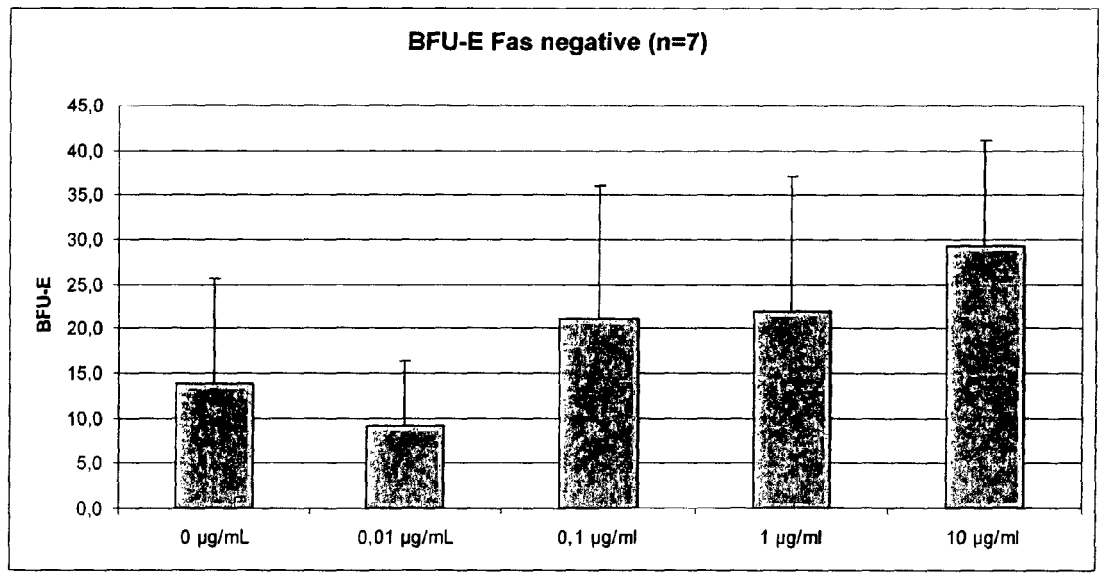

FIG. 11: Effect of APG101 on BFU-E growth. A comparison between Fas-positive and Fas-negative MDS.

Figure 12:
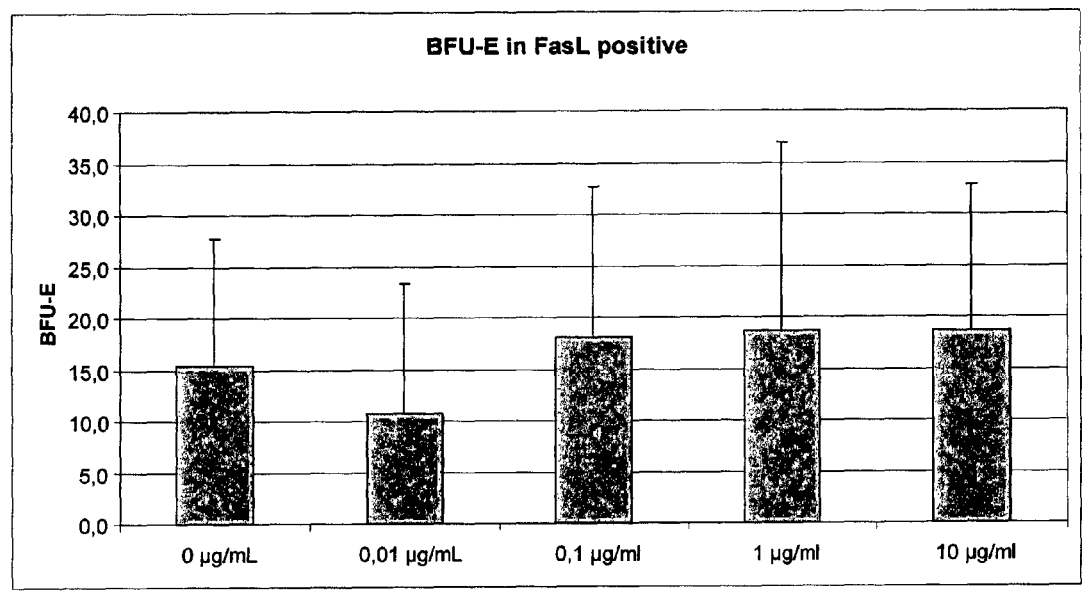
Figure 12:
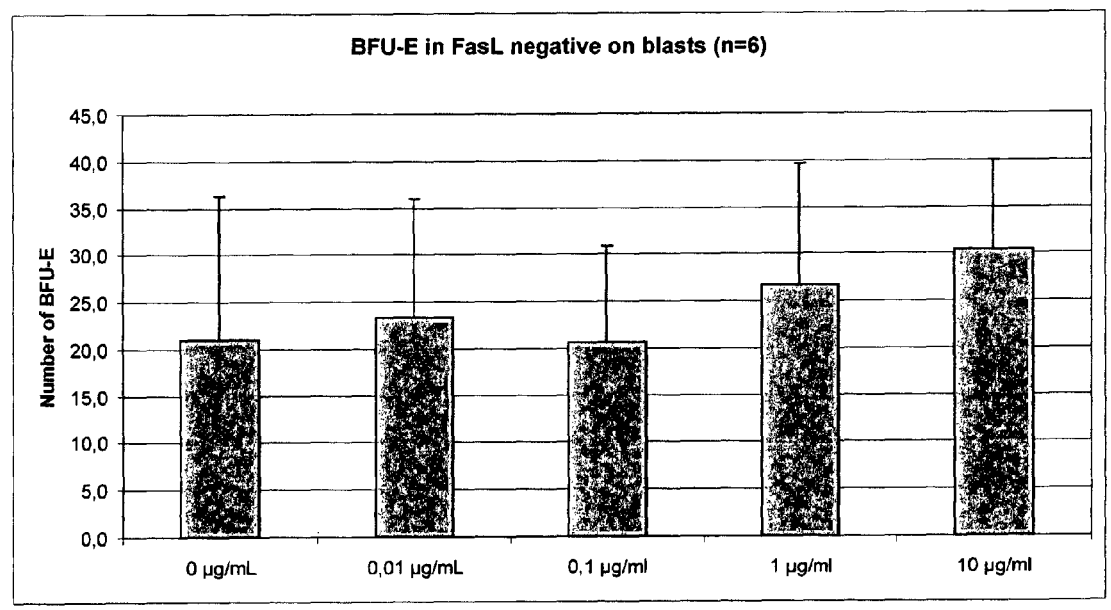

FIG. 12: Effect of APG101 according to FasL expression on CD45low cells.

Figure 13:
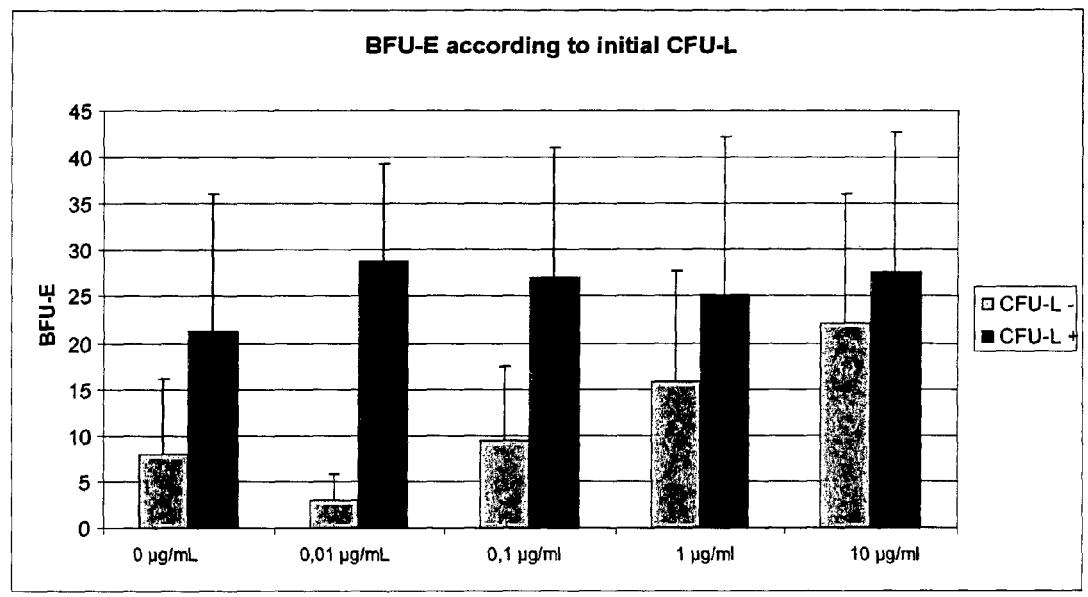
Figure 13:
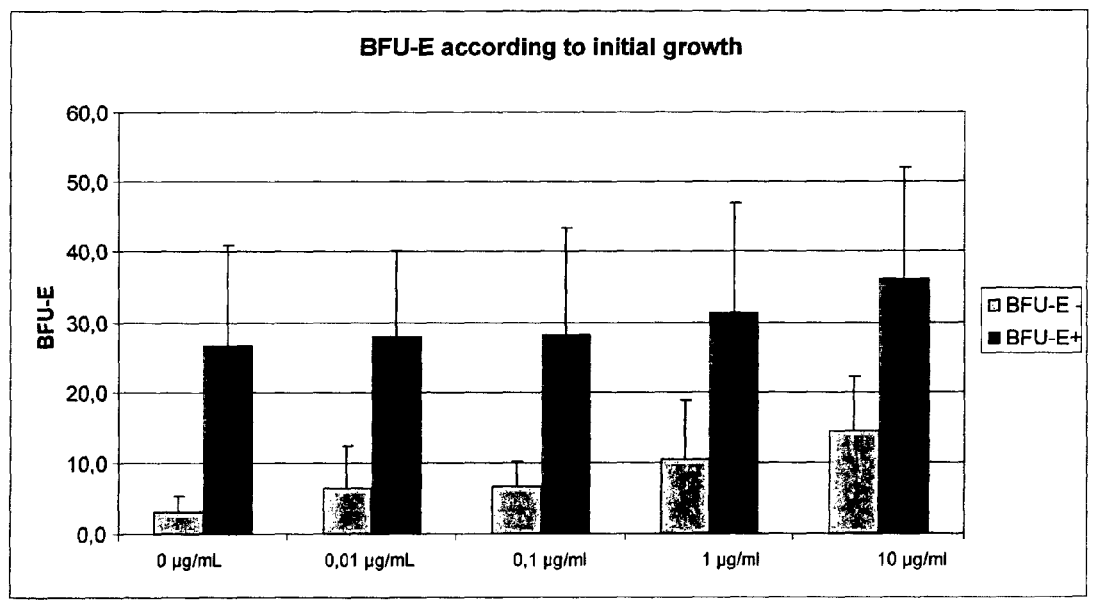

FIG. 13: Effect of APG101 on BFU-E growth according to CFU-L and BFU-E growth at baseline.

MATERIALS AND METHODS

Lab Materials

| Description | Lot | Supplier |
|---|---|---|
| Stable purified trimer of CD95ligand (CD95L-T4) APG101 | | Apogenix |
| Cytokines | SCF 02630 | Promega |
| SCF, IGF-1 | IGF-1 | SIGMA |
| Methylcellulose | 04100 | Stem Cell technologies |
| Culture medium IDMD glutamax | 31980-022 | Invitrogen |
| Fluorochrome-labelled antibodies and proteins | CD95 clone UB2 IM1506 CD235a (GPA)clone 11E4B IM2212 CD71 clone YDJ1.2.2 IM0483 | Beckman Coulter |

Bone Marrow Samples

Normal and MDS bone marrow samples were collected from patients of the Cochin Hospital, Paris and from related departments that are associated to multicenter biological studies coordinated by Prof. M. Fontenay by sternal aspiration. Patients had given their informed consent for cellular biology and genetic studies before bone marrow aspiration according to the recommendations of the local ethics committee Equipment

| Name | Internal Identification Number |
|---|---|
| MIDI Macs column | Milteny Biotech |
| FC 500 flow cytometer | Beckman Coulter |
| Incubators (5% $CO_2$, 37° C.) | Jouan |
| Microscope | Zeiss |

Methods
Relevant SOPs

Current SOP in the lab are referred and validated in the Guide de Bonne Exécution des Analyses de Bioloige médicale by M. Fontenay and C. Lacombe in 2002.

| SOP | Nr. | Release Date |
|---|---|---|
| CD34+ cell isolation | GBEA2v1 | Jan. 2, 2002 |
| Erythroid progenitor culture | GBEA2v1 | Jan. 2, 2002 |
| Methylcellulose assays | GBEA1v1 | Jan. 2, 2002 |

Tools and Platforms
APG101 Fas-Fc chimera (Apogenix): an inhibitor of Fas-dependent apoptosis; provided by Apogenix GmbH.
CD95L-T4: trimeric ligand for Fas provided by Apogenix
Erythroid cell cultures were performed as described: Bone marrow CD34$^+$ cells were isolated on MIDI Macs column and cultured in SCF, Epo, IGF-1 and dexamethasone to induce CD34+ cell commitment to the erythroid lineage and target erythroid cell proliferation. After 10 days, erythroid cell terminal maturation is obtained by switching cells to Epo and insulin containing medium.
Flow cytometry was used to quantify erythroid cell maturation during in vitro liquid culture.

Protocols
Flow Cytometry

Subpopulations of cells were identified by double labelling using monoclonal antibodies to CD71 (transferrin receptor) and glycophorin a (GPA CD235a). The different stages of maturation were CD71−/GPA−, CD71+/GPA−, CD71+/GPA+ and finally CD71−/GPA+ cells. Membrane Fas expression was quantified by CD95 labelling and expression as ratio of median fluorescence intensity to isotypic control (RFI). Receiver operating curve (ROC) analysis that is a graphical representation of the relationship between the true positive ratio and the false positive ratio for a range of cutoff values was used to compare 132 MDS to 25 controls demonstrated that the threshold of positivity was a RFI of 1.8. Apoptosis was measured by Annexin v/7-AAD labelling. Samples were analyzed on FC500 apparatus (Beckman Coulter).

Cell Isolation and Culture

Bone marrow samples from patients and healthy control subjects were collected by sternal aspiration and CD34+ cells were purified (>85% CD34+ cells) on MIDI-MACS immunoaffinity columns (Miltenyi Biotech, Bergisch Gladbach, Germany) (Claessens et al, 2002). Purified CD34+ cells were cultured in Dulbecco modified Eagle medium (DMEM) containing 20% BIT (bovine serum albumin, insulin, holotransferrin), and appropriate cytokines: 50 ng/mL stem cell factor (SCF), 1 IU/mL erythropoietin (Epo), 40 ng/mL insulin-like growth factor 1 (IGF-1), and $10^{-6}$ M dexamethasone up to day 10 of culture, and 1 IU/mL Epo and $10^{-6}$ M insulin thereafter. An overview of the cultivation steps is shown in FIG. 3. The cells actively divided up to day 10 and showed little erythroid maturation. After changing the cytokines, most cells were differentiated erythroblasts by day 14.

Induction of Apoptosis by CD95L-T4 in Normal Erythroid Cells

Normal erythroid cells were treated with increasing concentrations of CD95L-T4. At a given concentration, the impact of CD95L-T4—added at early phase of erythroid cell commitment—on erythroid cell growth (BFU-E and overall amplification of erythroid precursors) was measured. The impact of CD95L-T4—added before the onset of caspase-3 activation preceding erythroid maturation was tested. Caspase-3 and targets were followed by flow cytometry and Western blot analysis.

Considering the 1/1 stoechiometry of the CD95L-T4/APG101 complex with a 11 nM binding affinity in humans, the concentration of CD95L-T4 and APG101 to be tested in the culture were in the same range (0.01 to 10 μg/ml).

Inhibition of CD95L-T4-Induced Apoptosis by APG101 in Normal Erythroid Cells

Normal erythroid cells were pre-treated with APG101 at increasing concentration before treatment with the previously determined concentration of CD95L-T4 either at the early phase of erythroid cell amplification or at the late phase of differentiation or both). Importantly, CD95L-T4 addition was avoided in samples with high levels of apoptosis at baseline. Effects of APG101 were evaluated on overall erythroid cell amplification, BFU-E growth, apoptosis, caspase-3 activity, caspase-3 target cleavage, and differentiation (GPA, cytology).

Inhibition of MDS Erythroid Cell Apoptosis by APG101

Increasing concentrations of APG101 (0.001 to 100 μg/ml) were tested
  on the number of BFU-E in clonogenic assays
  on the rate of amplification
  on apoptosis (caspase-3 activity, phosphatidylserine exposure, caspase-3 targets)
  on erythroid cell differentiation (GPA/CD71, cytological examination, erythroid gene expression in microarrays).

It was previously shown that Fas is overexpressed on the bone marrow CD34$^+$ cell fraction. Therefore a comparison was made between erythroid and granulocytic progenitor cells in MDS samples in specific culture conditions for each lineage. It was tested whether treatment with APG101 restores normal kinetics of caspase-3 activity and prevents caspase-3 target cleavage.

Methylcellulose Assay

Mononuclear cells isolated from the bone marrow aspirates after Ficoll gradient were seeded in 0.8% methylcellulose containing fetal calf serum, BSA and cytokines (IL3 0.1 UI/ml, IL6 10 ng/ml, GM-CSF 5 ng/ml, EPO 1 UI/ml, and SCF 20 ng/ml at a concentration of $10^6$ cells/ml). CFU-E and CFU-L were counted at day 7 of the culture and BFU-E and CFU-GFM were counted at day 14. Increasing concentrations of APG101 were added.

Statistics

Biological data were analyzed as median values±standard error of the mean. Sensitivity and specificity of flow cytometry for Fas and FasL assays were evaluated with the Receiver Operating Curve (ROC) and the threshold value was deduced. Continuous variables were compared with the Student t-test (Excel 2003 software, Microsoft). The Kaplan-Meier estimator was used to evaluate the impact of Fas and FasL on overall survival over time, in two subgroups of the population under study, and compared with the Log-Rank test. All statistical analyses were 2-sided and P-values less than 0.05 were considered to be significant. Statistical analyses were performed using the GraphPad software.

Results

FasL Expression and MDS Diagnosis

The expression of FasL was measured both in CD45low/CD34+ and CD71+ bone marrow cell populations in 84 MDS, 21 sAML and 17 controls. FasL was significantly more elevated in MDS than sAML or controls (FIG. 4A) and according to ROC, the threshold of positivity was 6. When comparing MDS to controls, the predictive value of FasL expression to discriminate between MDS and controls was good (area under the curve: 0.73; P=0.002; FIG. 4B).

Clinical information was collected for 166 MDS or sAML patients with known value of Fas expression at diagnosis and in 42 MDS/sAML patients with known value of FasL at diagnosis to analyze the impact of Fas or FasL expression on prognosis. In the group of 166 MDS patients, 41% were positive for Fas and did not demonstrate any difference in terms of age, sex, hemogram parameters, % bone marrow blasts, multilineage dysplasia, karyotype, IPSS and treatments. Fas expression had no impact on overall survival (FIG. 5). In addition, Fas expression was not predictive of the response to EPO.

In the group of 42 patients with MDS/sAML, 18 patients were positive for FasL (RFI≥5). Hb level and median of overall survival were equivalent in FasL-positive and FasL-negative patient (P=0.57 and P=0.97, respectively). In addition, FasL expression in a small cohort of patients (n=22) was not predictive of the response to treatment.

In summary, these data show that Fas and FasL were overexpressed in MDS, and FasL overexpression is predictive of MDS. Neither Fas-expression nor FasL-expression are prognostic parameters for overall survival.

Effect of APG101 on Hematopoietic Progenitor Growth

Studies have shown that blocking FasL with an excess of soluble Fas (Fas: Fc) as well as the disruption of Fas signaling through ectopic expression of a dominant negative form of the adapter FADD rescued BFU-E growth. When analyzing the effect of increasing concentrations of APG101 (0, 0.01, 0.1, 1, 10 μg/ml) on erythroid and granulo-monocytic progenitors in methylecellulose assays it became evident that APG101 did not stimulate CFU-GM growth while a moderate positive effect was noticed on BFU-E growth (FIG. 6).

In addition the effect of APG101 on mature erythroid progenitor growth (CFU-E) and the response of leukemic blasts was analyzed by counting the number of CFU-L (non erythroid clusters of at least 50 cells) at day 7 of the methylcellulose culture (FIG. 7). It was found that APG101 did not rescue CFU-E growth and did not increase the number of CFU-L even in samples from RAEB2 patients (MDS with more than 10% blasts at diagnosis) suggesting that APG101 does not stimulate the growth of leukemic blasts.

To get further insight into the effect of APG101 on MDS erythropoiesis, CD34+ bone marrow cells from MDS patient were isolated and seeded under "erythroid conditions" for commitment. Cells were harvested at day 5 of the liquid culture and then seeded in methylcellulose to evaluate the number of BFU-E and CFU-GM. As shown in FIG. 7, the initial number of BFU-E was reduced in MDS compared to controls. APG101 induced a 3-fold increase of the number of BFU-E without reaching a normal level. CFU-GM were less severely impaired than BFU-E and were not affected by APG101. These results suggest a specific effect of APG101 on the erythroid lineage.

To test the effect of APG101 on the differentiation of cells during erythropoiesis different concentrations of APG101 were added to the cell culture when the culture was switched to Epo & insulin. which coincidates with the onset of FasL expression. At day 14 of the culture the overall cell number was increased by a mean of 60% and apoptosis appeared to be reduced up to 33% (FIG. 9).

APG101 had no effect on erythroid cell differentiation, more importantly it did not block cell maturation (FIG. 10).

To delineate the group of patients that could benefit from the drug, data from methy-cellulose assays were re-analyzed according to initial clinical and biological characteristics. Methylcellulose assays were previously validated as a useful tool for predicting the response to Epo and correlated well with the quality of erythropoiesis (Frisan et al, 2010).

First the clonogenic assays were analyzed according to the initial expression of Fas. As shown in FIG. 11, the improvement of BFU-E growth in the presence of 10 μg/ml APG101 was not significantly different in Fas-positive and Fas-negative patients.

Next, the effect of APG101 was analyzed according to the expression of FasL on the CD71-positive population. In this series, the threshold of positivity was 2.8. FasL-positive MDS had a median fasL RFI of 3.7 and FasL-negative patients had a median FasL RFI of 2.2. The effect of APG101 did not differ between FasL-positive patients showing high-FasL-expression and FasL-negative patients showing low FasL-expression.

Third, a possible correlation between the effect of APG101 on the BFU-E growth and the initial growth of CFU-L at diagnosis was sought. In patients with excess of leukemic clusters, APG101 failed to rescue BFU-E growth while it very efficiently increased the number of BFU-E in patients with low initial growth of CFU-L (FIG. 13, left).

Finally, APG101 more efficiently improved BFU-E growth in bone marrow cells from MDS patients with severe alteration of erythropoiesis at baseline than in patients with preserved erythropoiesis (FIG. 13, right).

SUMMARY

It was demonstrated that in the in vitro culture of hematopoietic stem cells (CD34+ cells) from low and INT-1 grade MDS patients with severe impairment of erythropoiesis APG101 rescues erythroid cell growth. APG101 did not promote the growth of leukemic cells and thus did not increase the risk of leukemic cell expansion.

Overexpression of FasL was predictive of the disease. However, neither Fas nor FasL expression was clearly demonstrated to have an impact on overall survival.

Fas is one of the main actors of apoptotic cell death of hematopoietic precursor cells resulting in anemia Thus, inhibiting Fas and FasL interaction using soluble Fas receptor (i.e. APG1010) could rescue erythropoiesis in MDS patients.

APG101 rescues erythroid cell growth in the subgroup of MDS patients with a severe defect of erythropoiesis and without an excess of leukemic blasts. APG101 did not stimulate the growth of leukemic cells as assessed by counting CFU-L, however, APG101 was unable to rescue BFU-E growth in patients presenting with an excess of CFU-L at diagnosis. Together, APG101 is effective in rescuing BFU-E growth in hematopoietic stem cells from patients with MDS with severe impairment of erythropoiesis at diagnosis and without excess of blasts. These patients were previously identified to be resistant to erythropoiesis-stimulating agents (ESA) in part due to overexpression of Fas and high level of apoptosis (Frisan et al, 2010).

LITERATURE

Bennett J M, Catovsky D, Daniel M T, Flandrin G, Galton D A, Gralnick H R, et al. Proposals for the classification of the myelodysplastic syndromes. Br. J. Haematol. 1982 June; 51(2):189-199.

Bouscary D, De Vos J, Guesnu M, Jondeau K, Viguier F, Melle J, Picard F, Dreyfus F, Fontenay-Roupie M. *Fas/Apo-1 (CD95) expression and apoptosis inpatients with myelodysplastic syndromes*. Leukemia. 1997 Jun.; 11(6): 839-45.

Carlile G W, Smith D H, Wiedmann M. *Caspase-3 has a nonapoptotic function in erythroid maturation*. Blood. 2004 Jun. 1; 103(11):4310-6.

Claessens Y E, Bouscary D, Dupont J M, et al. In vitro proliferation and differentiation of erythroid progenitors from patients with myelodysplastic syndromes: evidence for Fas-dependent apoptosis. Blood. 2002; 99: 1594-1601.

Claessens Y E, Park S, Dubart-Kupperschmitt A, Mariot V, Garrido C, Chrétien S, Dreyfus F, Lacombe C, Mayeux P, Fontenay M. *Rescue of early-stage myelodysplastic syndrome-deriving erythroid precursors by the ectopic expression of a dominant-negative form of FADD*. Blood. 2005 May 15; 105(10):4035-42.

De Maria R, Zeuner A, Eramo A, Domenichelli C, Bonci D, Grignani F, Srinivasula S M, Alnemri E S, Testa U, Peschle C. *Negative regulation of erythropoiesis by caspase-mediated cleavage of GATA-1*. Nature. 1999 Sep. 30; 401(6752):489-93.

Frisan E, Pawlikowska P, Pierre-Eugène C, Viallon V, Gibault L, Park S, Mayeux P, Dreyfus F, Porteu F, Fontenay M. *p-ERK1/2 is a predictive factor of response to erythropoiesis-stimulating agents in low/int-1 myelodysplastic syndromes*. Haematologica. 2010 November; 95(11):1964-8.

Greenberg P, Cox C, LeBeau M M, Fenaux P, Morel P, Sanz G, Sanz M, Vallespi T, Hamblin T, Oscier D, Ohyashiki K, Toyama K, Aul C, Mufti G, Bennett J. *International scoring system for evaluating prognosis in myelodysplastic syndromes*. Blood. 1997 Mar. 15; 89(6):2079-88.

Liu Y, Pop R, Sadegh C, Brugnara C, Haase V H, Socolovsky M. *Suppression of Fas-FasL coexpression by erythropoietin mediates erythroblast expansion during the erythropoietic stress response in vivo*. Blood. 2006 Jul. 1; 108(1):123-33.

Ribeil J A, Zermati Y, Vandekerckhove J, Cathelin S, Kersual J, Dussiot M, Coulon S, Moura I C, Zeuner A, Kirkegaard-Sørensen T, Varet B, Solary E, Garrido C, Hermine O. *Hsp70 regulates erythropoiesis by preventing caspase-3-mediated cleavage of GATA-1*. Nature. 2007 Jan. 4; 445(7123):102-5.

Socolovsky M, Murrell M, Liu Y, Pop R, Porpiglia E, Levchenko A. *Negative autoregulation by FAS mediates robust fetal erythropoiesis*. PLoS Biol. 2007 Oct.; 5 (10):e252.

Tehranchi R, Fadeel B, Forsblom A M, et al. Granulocyte colony-stimulating factor inhibits spontaneous cytochrome c release and mitochondria-dependent apoptosis of myelodysplastic syndrome hematopoietic progenitors. Blood. 2003; 101: 1080-1086.

Vardiman J W, Thiele J, Arber D A, Brunning R D, Borowitz M J, Porwit A, Harris N L, Le Beau M M, Hellström-Lindberg E, Tefferi A, Bloomfield C D. *The 2008 revision of the World Health Organization (WHO) classification of myeloid neoplasms and acute leukemia: rationale and important changes*. Blood. 2009 Jul. 30; 114(5):937-51.

Zermati Y, Garrido C, Amsellem S, et al. Caspase activation is required for terminal erythroid differentiation. J Exp Med. 2001; 1 93: 247-254.

The invention claimed is:

1. A method for treating myelodysplastic syndrome (MDS) in a patient, comprising the step of administering a fusion protein APG101 comprising an extracellular CD95R domain having the amino acid sequence 26-172 of SEQ ID NO: 1 and a human Fc domain having the amino acid sequence 172-400 of SEQ ID NO: 1 to a patient in need thereof, wherein the MDS is selected from the IPSS low-risk MDS subgroup and/or the IPSS intermediate-1 (int-1) risk MDS subgroup, and the fusion protein binds to CD95 ligand (CD95L) and inhibits CD95 signalling pathway.

2. The method according to claim 1, wherein the MDS population is characterized by increased apoptosis during erythropoiesis.

3. The method according to claim 1, wherein the MDS population is characterized by a severe defect of erythropoiesis without an excess of blasts.

4. The method according to claim 1, wherein the MDS population is characterized by being resistant to erythropoiesis stimulating agents (ESA) and/or colony stimulating factors.

5. The method according to claim 1, wherein the fusion protein is administered in a pharmaceutical composition comprising pharmaceutically acceptable carriers, diluents and/or adjuvants.

6. The method according to claim 1, wherein the fusion protein is administered in a pharmaceutical composition comprising at least one further active ingredient of an erythropoiesis stimulating agent and/or an apoptosis inhibiting agent.

7. The method according to claim 1, wherein the fusion protein is administered at a total amount of 50 to 400 mg/week.

8. The method according to claim 7, wherein the fusion protein is administered at a total amount of 100 to 200 mg/week.

* * * * *